United States Patent
Ding et al.

(10) Patent No.: US 10,513,727 B2
(45) Date of Patent: Dec. 24, 2019

(54) MULTIPLEX PYROPHOSPHOROLYSIS ACTIVATED POLYMERIZATION TO AMPLIFY MULTIPLE ALMOST-SEQUENCE-IDENTICAL TEMPLATES IN A SINGLE REACTION

(71) Applicants: Shaofeng Ding, Santa Fe Springs, CA (US); Qiang Liu, Upland, CA (US)

(72) Inventors: Shaofeng Ding, Santa Fe Springs, CA (US); Qiang Liu, Upland, CA (US)

( * ) Notice: Subject to any disclaimer, the term of this patent is extended or adjusted under 35 U.S.C. 154(b) by 238 days.

(21) Appl. No.: 15/462,342

(22) Filed: Mar. 17, 2017

(65) Prior Publication Data
US 2018/0265919 A1 Sep. 20, 2018

(51) Int. Cl.
*C12Q 1/6853* (2018.01)
*C12Q 1/6858* (2018.01)
*C07H 21/04* (2006.01)

(52) U.S. Cl.
CPC ......... *C12Q 1/6853* (2013.01); *C12Q 1/6858* (2013.01)

(58) Field of Classification Search
None
See application file for complete search history.

(56) References Cited

U.S. PATENT DOCUMENTS

2014/0329245 A1* 11/2014 Spier .................. C12Q 1/686
435/6.12

OTHER PUBLICATIONS

Gen Bank Accession No. AH002919, publicly available 2016 [retrieved on-line at: https://www.ncbi.hlm.nih.gov/nucleotide/AH002919.2?report=genbank&log$=nuclalign&blast_rank=56KUJMB8014; retrival date Jan. 31, 2019]. (Year: 2016).*
Song et al., "Real-Time Bidirectional Pyrophosphorolysis-Activated Polymerization for Quantitative Detection of Somatic Mutations," PLoS One, April, vol. 9, No. 4, e96420, pp. 1-9 (Year: 2014).*
GenBank Accession No. NM_001346941 [retrieved on-line Jun. 18, 2019, publicly available May 28, retrieved from: https:// www.ncbi.nlm.nih.gov/nucleotide/NM_001346941.1?report=genbank&log$=nuclalign&blast_rank=1&RID=GJGSVKN9014] (Year: 2019).*
Song et al., "Real-Time Bidirectional Pyrophosphorolysis-Activated Polymerization for Quantitative Detection of Somatic Mutations," PLoS One, April, vol. 9, No. 4, e96420, Supplemental Data Table 1, p. 1. (Year: 2014).*

* cited by examiner

*Primary Examiner* — Young J Kim

(57) ABSTRACT

Through a novel primer design, multiplex pyrophosphorolysis activated polymerization uses multiple pairs of blocked primers to amplify multiple almost-sequence-identical templates located in one locus in a single reaction, greatly increasing the productivity of nucleic acid amplification.

16 Claims, 6 Drawing Sheets

Specification includes a Sequence Listing.

Complementarities      No. mismatch

COSM 6255 template

```
COSM 6255 primer       5'AGTGAACATTCC..>         2
Starting template      3'tcaatttaaggg....5'

COSM 6255 primer       5'AGTGAACATTCC..>         0
Duplicated template    3'tcaCttGtaaggg....5'

COSM12369 primer       5'AGGTACAATTCC..>         2
Starting template      3'tcaatttaaggg....5'

COSM12369 primer       5'AGGTACAATTCCCGT..>      4
Duplicated template    3'tcaCttGtaagggca....5'
```

|   |   | Complementarities | No. mismatch |
|---|---|---|---|
| COSM 6255 template | COSM 6255 primer<br>Starting template | 5'AGTGAACATTCC..><br>3'tcaattttaaggg....5' | 2 |
| | COSM 6255 primer<br>Duplicated template | 5'AGTGAACATTCC..≥<br>3'tcaCttGtaaggg....5' | 0 |
| | COSM12369 primer<br>Starting template | 5'AGGTACAATTCC..><br>3'tcaattttaaggg....5' | 2 |
| | COSM12369 primer<br>Duplicated template | 5'AGGTACAATTCCCGT..><br>3'tcaCttGtaagggca....5' | 4 |

Figure 1

|  | Complementarities | No. mismatch |
|---|---|---|
| COSM 6252 primer<br>Starting template | 5' ACTGCATTCAAA..><br>3' tgacttaagtttt....5' | 1 |
| COSM 6252 primer<br>Duplicated template | 5' ACTGCATTCAAA..><br>3' tgacGtaagtttt....5' | 0 |
| COSM 6253 primer<br>Starting template | 5' ACTGAAGTCAAA..><br>3' tgacttaagtttt....5' | 1 |
| COSM 6253 primer<br>Duplicated template | 5' ACTGAAGTCAAA..><br>3' tgacGtaagtttt....5' | 2 |
| COSM 6239 primer<br>Starting template | 5' CTGAATGCAAA..><br>3' tgacttaagtttt....5' | 1 |
| COSM 6239 primer<br>Duplicated template | 5' CTGAATGCAAA..><br>3' tgacGtaagtttt....5' | 2 |

(COSM 6252 template)

Figure 3

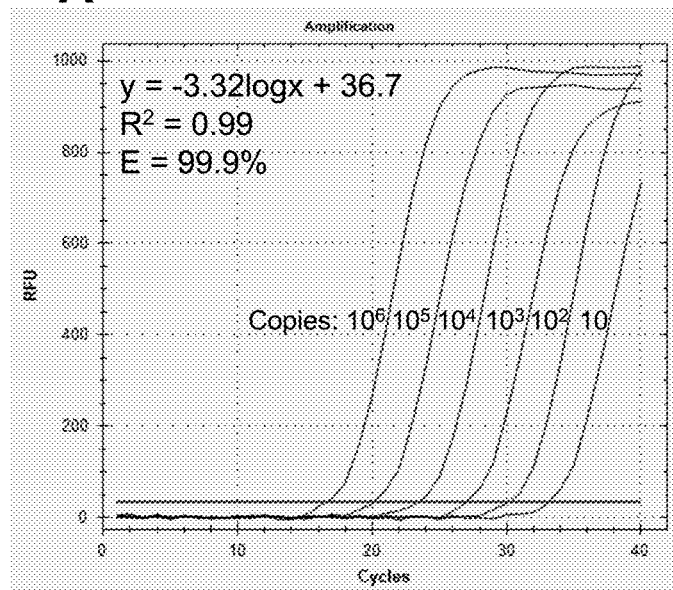
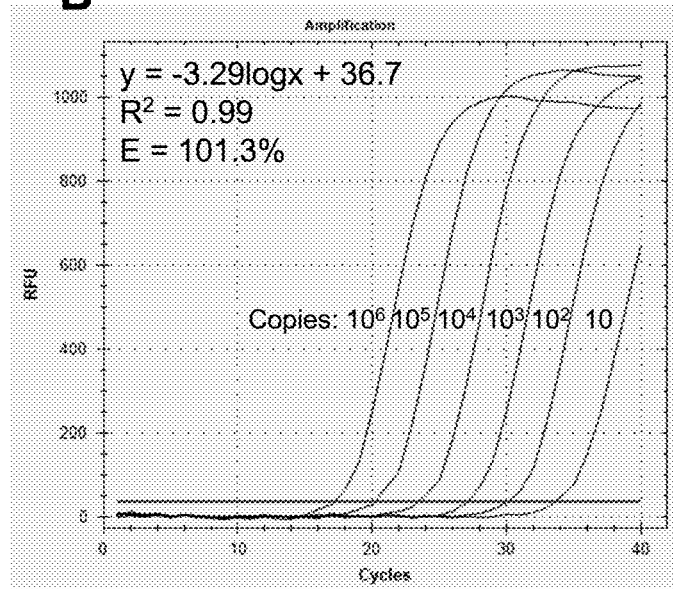
Figure 4

| | | Complementarities | No. mismatch |
|---|---|---|---|
| COSM 518 template | COSM 518 primer<br>Starting template | 5'CTGACTATAAAC..><br>3'gacttatatttga....5' | 1 |
| | COSM 518 primer<br>Duplicated template | 5'CTGACTATAAAC..><br>3'gactGatatttga....5' | 0 |
| | COSM 516 primer<br>Starting template | 5'CTGAATCTAAAC..><br>3'gacttatatttga....5' | 1 |
| | COSM 516 primer<br>Duplicated template | 5'CTGAAT CTAAAC..><br>3'gactG atatttga....5' | 2 |
| | COSM 517 primer<br>Starting template | 5'CTGAATATCAAC..><br>3'gacttatatttga....5' | 1 |
| | COSM 517 primer<br>Duplicated template | 5'CTGAATATCAAC..><br>3'gactGatatttga....5' | 2 |

Figure 5

SEQUENCE LISTING

<160> NUMBER OF SEQ ID NOS: 43

<210> SEQ ID NO 1
<211> LENGTH: 59
<212> TYPE: DNA
<213> ORGANISM: Homo sapiens

<400> SEQUENCE: 1
ggctaaaatt atccctgggc tctcagtaaa gccaattgat gtcatcactt ggacagtgt    59

<210> SEQ ID NO 2
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 2
ggctaaaatt atccctgggc tctcagtaan                                    30

<210> SEQ ID NO 3
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 3
acactgtcca agtgatgaca tcaattggcn                                    30

<210> SEQ ID NO 4
<211> LENGTH: 59
<212> TYPE: DNA
<213> ORGANISM: Homo sapiens

<400> SEQUENCE: 4
ggctaaaatt atccctgggc tctcagtaat gccaattgat gtcatcactt ggacagtgt    59

<210> SEQ ID NO 5
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 5
ggctaaaatt atccctgggc tctcagtaan                                    30

<210> SEQ ID NO 6
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 6
acactgtcca agtgatgaca tcaattggcn                                    30

<210> SEQ ID NO 7
<211> LENGTH: 59
<212> TYPE: DNA
<213> ORGANISM: Homo sapiens

<400> SEQUENCE: 7
ctgctcactg ctaatggggt tatgcggtta caagggcgtg catcatttcg cacacccag      59

<210> SEQ ID NO 8
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 8
ctgctcactg ctaatggggt tatgcggttn                                       30

<210> SEQ ID NO 9
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 9
ctgggtgtgc gaaatgatgc acgcccttgn                                       30

<210> SEQ ID NO 10
<211> LENGTH: 59
<212> TYPE: DNA
<213> ORGANISM: Homo sapiens

<400> SEQUENCE: 10
ctgctcactg ctaatggggt tatgcggttt caagggcgtg catcatttcg cacacccag      59

<210> SEQ ID NO 11
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 11
ctgctcactg ctaatggggt tatgcggttn                                       30

<210> SEQ ID NO 12
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a ddA

<400> SEQUENCE: 12
ctgggtgtgc gaaatgatgc acgcccttgn                                       30

<210> SEQ ID NO 13
<211> LENGTH: 64
<212> TYPE: DNA

```
<213> ORGANISM: Homo sapiens

<400> SEQUENCE: 13
agttaaaatt cccgtcgcta tcaaggaacc gaaagccaac aaggaaatcc tcgatgtgag      60
tttc                                                                   64

<210> SEQ ID NO 14
<211> LENGTH: 64
<212> TYPE: DNA
<213> ORGANISM: Homo sapiens

<400> SEQUENCE: 14
agtgaacatt cccgtcgcta tcaaggaacc gaaagccaac aaggaaatcc tcgatgtgag      60
tttc                                                                   64

<210> SEQ ID NO 15
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a ddC

<400> SEQUENCE: 15
agtgaacatt cccgtcgcta tcaaggaacn                                       30

<210> SEQ ID NO 16
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 16
gaaactcaca tcgaggattt ccttgttggn                                       30

<210> SEQ ID NO 17
<211> LENGTH: 67
<212> TYPE: DNA
<213> ORGANISM: Homo sapiens

<400> SEQUENCE: 17
agttaaaatt cccgtcgcta tcaaggaatc tccgaaagcc aacaaggaaa tcctcgatgt      60
gagtttc                                                                67

<210> SEQ ID NO 18
<211> LENGTH: 67
<212> TYPE: DNA
<213> ORGANISM: Homo sapiens

<400> SEQUENCE: 18
aggtacaatt cccgtcgcta tcaaggaatc tccgaaagcc aacaaggaaa tcctcgatgt      60
gagtttc                                                                67

<210> SEQ ID NO 19
<211> LENGTH: 31
<212> TYPE: DNA
<213> ORGANISM: Homo sapiens
<220> FEATURE:
<221> NAME/KEY: misc_feature
```

```
<222> LOCATION: (31)..(31)
<223> OTHER INFORMATION: n is ddT

<400> SEQUENCE: 19
aggtacaatt cccgtcgcta tcaaggaatc n                              31

<210> SEQ ID NO 20
<211> LENGTH: 55
<212> TYPE: DNA
<213> ORGANISM: Homo sapiens

<400> SEQUENCE: 20
actgaattca aaaagatcaa agtgctgagc tccggtgcgt tcggcacggt gtata     55

<210> SEQ ID NO 21
<211> LENGTH: 55
<212> TYPE: DNA
<213> ORGANISM: Homo sapiens

<400> SEQUENCE: 21
actgcattca aaaagatcaa agtgctgagc tccggtgcgt tcggcactgt gtata     55

<210> SEQ ID NO 22
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 22
actgcattca aaaagatcaa agtgctgn                                  28

<210> SEQ ID NO 23
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 23
tatacacagt gccgaacgca ccggagcn                                  28

<210> SEQ ID NO 24
<211> LENGTH: 55
<212> TYPE: DNA
<213> ORGANISM: Homo sapiens

<400> SEQUENCE: 24
actgaattca aaaagatcaa agtgctgtgc tccggtgcgt tcggcacggt gtata     55

<210> SEQ ID NO 25
<211> LENGTH: 55
<212> TYPE: DNA
<213> ORGANISM: Homo sapiens

<400> SEQUENCE: 25
actgaagtca aaaagatcaa agtgctgtgc tccggtgcgt tcggcaaggt gtata     55

<210> SEQ ID NO 26
<211> LENGTH: 28
<212> TYPE: DNA
```

```
<213> ORGANISM: Homo sapiens
<220> FEATURE:
<221> NAME/KEY: misc_feature
<222> LOCATION: (28)..(28)
<223> OTHER INFORMATION: n is ddT

<400> SEQUENCE: 26
actgaagtca aaagatcaa agtgctgn                                          28

<210> SEQ ID NO 27
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddA

<400> SEQUENCE: 27
tatacacctt gccgaacgca ccggagcn                                         28

<210> SEQ ID NO 28
<211> LENGTH: 55
<212> TYPE: DNA
<213> ORGANISM: Homo sapiens

<400> SEQUENCE: 28
ctgaattcaa aaagatcaaa gtgctggcct ccggtgcgtt cggcacggtg tataa           55

<210> SEQ ID NO 29
<211> LENGTH: 55
<212> TYPE: DNA
<213> ORGANISM: Homo sapiens

<400> SEQUENCE: 29
ctgaatgcaa aaagatcaaa gtgctggcct ccggtgcgtt cggcacgatg tataa           55

<210> SEQ ID NO 30
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddC

<400> SEQUENCE: 30
ctgaatgcaa aaagatcaaa gtgctggn                                         28

<210> SEQ ID NO 31
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddG

<400> SEQUENCE: 31
ttatacaacg tgccgaacgc accggagn                                         28

<210> SEQ ID NO 32
<211> LENGTH: 59
<212> TYPE: DNA
<213> ORGANISM: Homo sapiens

<400> SEQUENCE: 32
```

-continued ctgaatataa acttgtggta gttggagctc gtggcgtagg caagagtgcc ttgacgata      59

<210> SEQ ID NO 33
<211> LENGTH: 59
<212> TYPE: DNA
<213> ORGANISM: Homo sapiens

<400> SEQUENCE: 33
ctgactataa acttgtggta gttggagctc gtggcgtagg caagagtgca ttgacgata      59

<210> SEQ ID NO 34
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddC

<400> SEQUENCE: 34
ctgactataa acttgtggta gttggagctn      30

<210> SEQ ID NO 35
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddG

<400> SEQUENCE: 35
tatcgtcaat gcactcttgc ctacgccacn      30

<210> SEQ ID NO 36
<211> LENGTH: 59
<212> TYPE: DNA
<213> ORGANISM: Homo sapiens

<400> SEQUENCE: 36
ctgaatataa acttgtggta gttggagctt gtggcgtagg caagagtgcc ttgacgata      59

<210> SEQ ID NO 37
<211> LENGTH: 59
<212> TYPE: DNA
<213> ORGANISM: Homo sapiens

<400> SEQUENCE: 37
ctgaatctaa acttgtggta gttggagctt gtggcgtagg caagagtgcc tttacgata      59

<210> SEQ ID NO 38
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 38
ctgaatctaa acttgtggta gttggagctn      30

<210> SEQ ID NO 39
<211> LENGTH: 30
<212> TYPE: DNA

```
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 39
tatcgtaaag gcactcttgc ctacgccacn                                          30

<210> SEQ ID NO 40
<211> LENGTH: 59
<212> TYPE: DNA
<213> ORGANISM: Homo sapiens

<400> SEQUENCE: 40
ctgaatataa acttgtggta gttggagcta gtggcgtagg caagagtgcc ttgacgata         59

<210> SEQ ID NO 41
<211> LENGTH: 59
<212> TYPE: DNA
<213> ORGANISM: Homo sapiens

<400> SEQUENCE: 41
ctgaatatca acttgtggta gttggagcta gtggcgtagg caagagtgcc ttgtcgata         59

<210> SEQ ID NO 42
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddA

<400> SEQUENCE: 42
ctgaatatca acttgtggta gttggagctn                                          30

<210> SEQ ID NO 43
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddT

<400> SEQUENCE: 43
tatcgacaag gcactcttgc ctacgccacn                                          30
```

MULTIPLEX PYROPHOSPHOROLYSIS ACTIVATED POLYMERIZATION TO AMPLIFY MULTIPLE ALMOST-SEQUENCE-IDENTICAL TEMPLATES IN A SINGLE REACTION

SEQUENCE LISTING

This application is being filed along with a Sequence Listing and its electronic format entitled SequenceListing.txt.

BACKGROUND OF THE INVENTION

Field of the Invention

The present invention relates to the field of molecular biology and particularly pyrophosphorolysis activated polymerization (PAP) for nucleic acid amplification.

Description of the Prior Art

PAP Technology for Nucleic Acid Amplification

Pyrophosphorolysis activated polymerization (PAP) is a method for nucleic acid amplification where pyrophosphorolysis and polymerization are serially coupled by DNA polymerase using 3' blocked primers (Liu and Sommer, 2000; Liu and Sommer, 2004b). A primer is blocked at the 3' end with a non-extendable nucleotide (3' blocker), such as a dideoxynucleotide, and cannot be directly extended by DNA polymerase. When the 3' blocked primer anneals to its complementary DNA template, DNA polymerase can remove the 3' blocker from the 3' blocked primer in the presence of pyrophosphate or its analog, which reaction is called pyrophosphorolysis. The DNA polymerase can then extend the 3' unblocked primer on the DNA template. In addition to references cited herein, PAP has been described in U.S. Pat. Nos. 6,534,269, 7,033,763, 7,105,298, 7,238,480, 7,504,221, 7,914,995, and 7,919,253.

The serial coupling of pyrophosphorolysis and extension using the 3' blocked primer in PAP results in an extremely high selectivity (Liu and Sommer, 2004a; Liu and Sommer, 2004b) because a significant nonspecific amplification (Type II error) requires mismatch pyrophosphorolysis followed by mis-incorporation by the DNA polymerase, an event with a frequency estimated to be $3.3 \times 10^{-11}$.

The bi-directional form of PAP (Bi-PAP) is especially suitable for allele-specific amplification that uses two opposing 3' blocked primers with a single nucleotide overlap at their 3' ends (Liu and Sommer, 2004a; Liu and Sommer, 2004b). Bi-PAP can detect one copy of a mutant allele in the presence of $10^9$ copies of the wild type DNA without false positive amplifications.

DNA-PAP

PAP was initially tested with Tfl and Taq polymerases using DNA template of the human dopamine D1 gene, proving the principle that DNA-dependent DNA pyrophosphorolysis and DNA-dependent DNA polymerization can be serially coupled (Liu and Sommer, 2000). The efficiency of PAP was greatly improved using TaqFS, a genetically engineered polymerase comprising a F667Y mutation, which were demonstrated using other DNA templates (Liu and Sommer, 2002).

RNA-PAP

RNA-PAP was developed that can directly amplify RNA template without additional treatment. RNA-PAP brings in a new mechanism for amplification of RNA template in which RNA-dependent DNA pyrophosphorolysis removes 3' blocker such as 3' dideoxynucleotide from a blocked primer when hybridized to RNA template, and then RNA-dependent DNA polymerization extends the activated primer. Due to this serial coupling, RNA-PAP has high selectivity against mismatches on the RNA template, providing highly specific amplification of RNA template (U.S. Pat. No. 9,133,491).

PAP with Acycolonucleotide Blocker and Type II Polymerase

We showed that Type II DNA polymerase efficiently catalyzes template-dependent pyrophosphorolysis to activate primers blocked at their 3' termini with acyclonucleotides in which a 2-hydroxyethoxymethyl group substitutes for the 2'-deoxyribofuranosyl sugar. Type II DNA polymerases Vent (exo-) and Pfu (exo-) were used for PAP with acyclonucleotide-blocked primers, besides Type I DNA polymerase (Liu and Sommer, 2004c).

Multiplex-PAP at Multiple Loci: Multiple Pairs of Primers Amplify Multiple Templates at Multiple Loci Advantageous to produce little or no primer-dimer or false priming (Liu and Sommer, 2002), multiple pairs of primers ($\geq 2$) were used to amplify multiple potential templates ($\geq 2$) located at multiple loci ($\geq 2$) in one reaction (Liu, et al., 2006). In an example, PAP used eight pairs of primers that targeted eight loci in human genome including seven different exons scattered along a 30 Kb sequence of the human factor IX gene and one exon in the human ATM gene.

Inhibitory Interaction in One-Locus-Duplex-PAP: Multiple Pairs of Primers Amplify Multiple Almost-Sequence-Identical Templates at one Locus We developed many Singleplex-PAP assays for detection of A/T biallelic polymorphisms in human genome, such as Rs4261 and Rs31224 loci. Each polymorphism contains an A or a T nucleotide exactly at the same nucleotide (Table 1).

For the biallelic polymorphism Rs4261, the first pair of blocked primers (SEQ ID No 2 and 3) were regularly designed as 5'-perfect-match primers, which match the A allelic template (SEQ ID 1), but mismatch the T allelic template at the 3' ends (SEQ ID 4) (Table 1). The Singleplex-PAP amplified the A allelic template, but extremely discriminated against the T allelic template.

The second pair of blocked primers (SEQ ID No 5 and 6) were also regularly designed as 5'-perfect-match primers, which match the T allelic template (SEQ ID 4), but mismatch the A allelic template at the 3' ends (SEQ ID 1). The Singleplex-PAP amplified the T allelic template (SEQ ID 4), but did not amplify the A allelic template (SEQ ID 1) at all.

The amplification efficiency of each Singleplex-PAP was measured to be >96% in serial dilution experiments in which the genomic template DNA was 10-fold serially diluted from $10^6$ to 10 copies per 20 ul of reaction.

However, when the two pairs of primers (SEQ ID No 2 and 3, 5 and 6), put together in one reaction, to amplify either or both of the two allelic templates (SEQ ID 1 and 4), the One-Locus-Duplex-PAP produced much less corresponding products with the amplification efficiencies 85-87%, leading to 16-fold less products by the end of the 30th cycle, thus indicating inhibitory interaction between the primers.

In another example of the biallelic polymorphism Rs4261, two pairs of blocked primers (SEQ ID No 8 and 9, 11 and 12) were regularly designed as 5'-perfect-match primers for the A and T alleles (SEQ ID 7 and 10) (Table 1). Similar tendencies of the inhibitory interaction were observed in amplification efficiencies, about 10% decreases per cycle between the Singleplex-PAP and One-Locus-Duplex-PAP.

With regularly designed 5'-perfect-match primers, this inhibitory interaction is common in One-Locus-Duplex-PAP. We hypothesize that competitive annealing of multiple almost-sequence-identical primers to their multiple almost-sequence-identical templates leads to the inhibition.

Advantages of the Invention of One-Locus-Multiplex-PAP

In order to amplify multiple potential almost-sequence-identical templates or alleles at one locus, a new design was developed that artificial mutations were introduced into multiple pairs of primers to reduce the inhibitory interaction and thus increase the amplification efficiencies.

TABLE 1

Inhibition in One-Locus-Duplex-PAP using 5'-perfect-match primers

| # | Locus [a] | Chromosome [a] | Bi-allelic template and primer | | Sequence (5' to 3') (SEQ ID NO) |
|---|---|---|---|---|---|
| 1 | Rs4261 | 7q | A allele | A-allelic template [b] | 5'ggctaaaattatccctgggctctcagtaaAgccaatt gatgtcatcacttggacagtgt3' (1) |
| | | | | A-Forward primer [c] | 5'GGCTAAAATTATCCCTGGGCTCT CAGTAAddA (2) |
| | | | | A-Reverse primer | 5'ACACTGTCCAAGTGATGACATC AATTGGCddT (3) |
| | | | T allele | T-allelic template | 5'ggctaaaattatccctgggctctcagtaaTgccaatt gatgtcatcacttggacagtgt3' (4) |
| | | | | T-Forward primer | 5'GGCTAAAATTATCCCTGGGCTCT CAGTAAddT (5) |
| | | | | T-Reverse primer | 5'ACACTGTCCAAGTGATGACATC AATTGGCddA (6) |
| 2 | Rs31224 | 5q | A allele | A-allelic template | 5'ctgctcactgctaatgggttatgcggttAcaaggg cgtgcatcatttcgcacacccag3' (7) |
| | | | | Forward primer | 5'CTGCTCACTGCTAATGGGGTTAT GCGGTTddA (8) |
| | | | | Reverse primer | 5'CTGGGTGTGCGAAATGATGCAC GCCCTTGddT (9) |
| | | | T allele | T-allelic template | 5'ctgctcactgctaatgggttatgcggttTcaaggg cgtgcatcatttcgcacacccag3' (10) |
| | | | | Forward primer | 5'CTGCTCACTGCTAATGGGGTTAT GCGGTTddT (11) |
| | | | | Reverse primer | 5'CTGGGTGTGCGAAATGATGCAC GCCCTTGddA (12) |

Footnotes of Table 1.
[a] From www.ncbi.nlm.nih.gov/snp/, Rs4261 is a A/T biallelic polymorphism and Rs31224 is another A/T biallelic polymorphism.
[b] The downstream strand is shown for the template Rs4261. The upper and bold case is the bi-allelic nucleotide.
[c] ddA, underlined, is a dideoxynucleotide located at the 3' end as a blocker. It matches the A allele-specific template Rs4261, but mismatched to the T allele-specific-template Rs4261 at the 3' end.

forward or reverse primer in the same direction as the above selected in the first pair is selected and has at least one artificial mutation introduced into its 5' region. In the template sequences, the artificial mutations of the selected primers in the first pair, the second pair and the third pair are located at different nucleotides.

The primers further comprise: c) the first pair of forward and reverse primers, in which the other of the forward and reverse primers is selected and has at least one artificial mutation introduced into the 5' region, and d) the second pair of forward and reverse primers, wherein the other of the

SUMMARY OF THE INVENTION

A plurality of pairs of forward and reverse blocked primers for pyrophosphorolysis activated polymerization to amplify a plurality of potential templates in one reaction, in which the template sequences are located at one locus in a genome and contain at least one nucleotide variance from each other, comprise: a) a first pair of forward and reverse primers to amplify a first template, in which the forward or reverse primers is selected and has at least one artificial mutation introduced into its 5' region, and b) a second pair of forward and reverse primers to amplify a second template, in which the corresponding forward or reverse primer in the same direction as the above selected primer in the first pair is selected and has at least one artificial mutation introduced into its 5' region. Furthermore, in the template sequences, the artificial mutations of the selected primers in the first pair and in the second pair are located at different nucleotides. In such a case inhibitory interactions among the primers are substantially reduced in the reaction.

The primers further comprise a third pair of forward and reverse primers to amplify a third template, in which the forward and reverse primers is selected and has at least one artificial mutation introduced into the 5' region. In the template sequences, the artificial mutations of the other selected primers in the first pair and in the second pair are located at different nucleotides.

For a pair of primers, the 3' regions, particularly the 3' ends, match the corresponding templates but mismatch the other templates.

For the forward or reverse primer of a pair, one artificial mutation is introduced into the 5' region.

For the forward or reverse primer of a pair, two artificial mutations are introduced into the 5' region.

The artificial mutations comprise six types of A to C, C to A, T to G, G to T, A to T, and T to A substitution mutations.

The artificial mutations result in four types of mismatches of G-A, C-T, A-A, T-T between the 5' regions of the primers and the complementary strands of the templates.

The artificial mutations comprise four types of A to C, C to A, T to G, and G to T substitution mutations which result in two types of mismatches of G-A and C-T between the 5' regions of the primers and the complementary strands of the templates.

The artificial mutations comprise two types of A to T and T to A substitution mutations which result in two types of mismatches of T-T and A-A between the 5' regions of the primers and the complementary strands of the templates.

The 5' regions of the primers range from the first to the twelfth nucleotide from the 5' ends.

The 5' regions of the primers range from the third to the ninth nucleotide from the 5' ends.

The artificial mutations of the forward or reverse primers are at different nucleotides in the template sequences.

The number of mismatches between the 5' region of a primer and the complementary strand of a starting template is the number of artificial mutations in the primer.

The maximum number of mismatches between the 5' region of a primer and the complementary strand of a duplicated template is two when one artificial mutation is introduced into each forward primer or each reverse primer.

The maximum number of mismatches between the 5' region of a primer and the complementary strand of a duplicated template is four when two artificial mutations are introduced into each forward primer or each reverse primer.

In any case, the minimum number of mismatches between the 5' region of a primer and the complementary strand of a duplicated template is zero.

The template sequences are completely or partially overlapped in the locus.

The template sequences contain at least one nucleotide variance from each other in the locus.

A method for pyrophosphorolysis activated polymerization comprise: a) providing a plurality of pairs of forward and reverse blocked primers to amplify a plurality of potential templates which sequences are at one locus in a genome and contain at least one nucleotide variance from each other, comprising: 1) a first pair of forward and reverse primers to amplify a first template, in which the forward or reverse primer is selected and has at least one artificial mutation introduced into its 5' region, and 2) a second pair of forward and reverse primers to amplify a second template, in which the corresponding forward or reverse primer in the same direction as the above selected primer in the first pair is selected and has at least one artificial mutation introduced into its 5' region, b) locating the artificial mutations of the selected primers in the first pair and the second pair at different nucleotides in the template sequences, and c) use the plurality of pairs of blocked primers to amplify the templates in one reaction.

BRIEF DESCRIPTION OF THE DRAWINGS

FIG. 1 shows how 5'-artificial-mismatch blocked primers work in One-Locus-Duplex-PAP in exon 19 of the EGFR gene. In the example, two pairs of primers were designed as 5'-artificial-mismatch primers COSM6255 and COSM12369 (SEQ ID No 15 and 16, 19 and 16) (Table 2). Only the 5' regions of the forward primers (SEQ ID 15 and 19) are diagramed with the complementary strands of the starting and duplicated templates COSM6255 (SEQ ID 13 and 14). Underlined and upper cases in the primer sequences are the artificial mutations. Underlined and upper cases in the duplicated template sequences are artificial mutations duplicated from the 5'-artificial-mismatch primers. The mismatch between the 5' region of a primer and the complementary strand of a template is indicated by rectangle frame. The number of mismatches is indicated for each case on the right side, showing different levels of complementarities.

FIG. 3 shows how 5'-artificial-mismatch primers work in One-Locus-Triplex-PAP in exon 18 of the EGFR gene. In the example, three pairs of primers were designed as 5'-artificial-mismatch primers COM6252, COSM6253 and COSM6239 (SEQ ID 22 and 23, 26 and 27, 30 and 31) (Table 4). Only the 5' regions of the forward primers (SEQ ID 22, 26 and 30) are diagramed with the complementary strands of the starting and duplicated templates COM6252 (SEQ ID 20 and 21).

FIG. 4 shows comparison of amplification efficiencies in exon 18 of the EGFR gene. In panel A, Singleplex-PAP used a pair of 5'-artificial-mismatch blocked primers COSM6252 (SEQ ID 22 and 23) to amplify the templates COSM6252 (SEQ ID 20 and 21) form plasmid DNA (Table 4). In panel B, One-Locus-Triplex-PAP used three pairs of primers COSM6252, COSM6253 and COSM6239 (SEQ ID 22 and 23, 26 and 27, 30 and 31) to amplify the templates COSM6252 (SEQ ID 20 and 21) form plasmid DNA.

FIG. 5 shows how 5'-artificial-mismatch primers work in One-Locus-Triplex-PAP in exon 2 of the KRAS gene. In the example, three pairs of primers were designed as 5'-artificial-mismatch primers COSM518, COSM516 and COSM517 (SEQ ID 34 and 35, 38 and 39, 42 and 43) (Table 6). Only the 5' regions of the forward primers (SEQ ID 34, 38 and 42) are diagramed with the complementary strands of the starting and duplicated templates COSM518 (SEQ ID 32 and 33).

DETAILED DESCRIPTION OF THE INVENTION

Terminology

Figure 2:
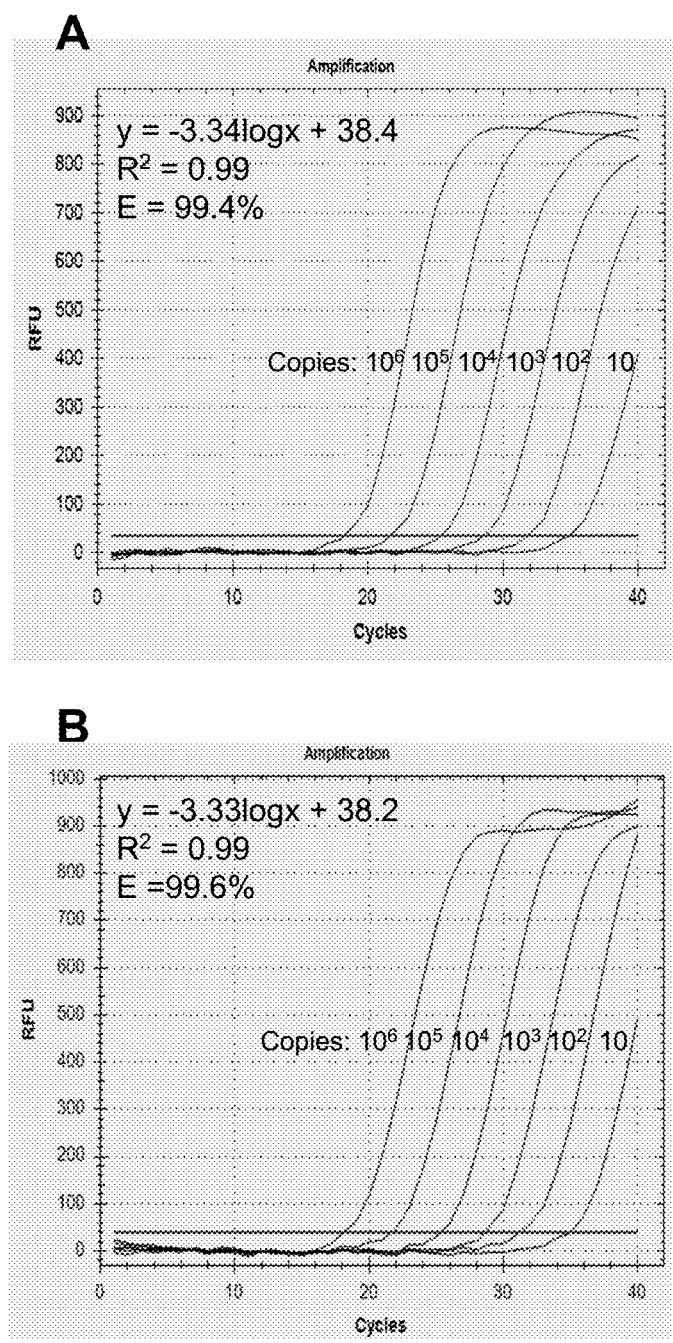
FIG. 2 shows comparison of amplification efficiencies in exon 19 of the EGFR gene. In panel A, Singleplex-PAP used a pair of 5'-artificial-mismatch blocked primers COSM6255 (SEQ ID No 15 and 16) to amplify the templates COSM6255 (SEQ ID 13 and 14) form plasmid DNA (Table 2). In panel B, One-Locus-Duplex-PAP used two pairs of primers COSM6255 and COSM12369 (SEQ ID No 15 and 16, 19 and 16) to amplify the templates COSM6255 (SEQ ID 13 and 14) form plasmid DNA. To determine the amplification efficiency, the template was 10-fold serially diluted from $10^6$ to 10 copies per 20 ul of reaction. Threshold line is also indicated. X-axis is the cycle number and Y-axis is the net fluorescence signal in arbitrary units. Amplification efficiencies of the Singleplex-PAP and One-Locus-Duplex-PAP were determined together with equations of linear regression and coefficients of determination ($R^2$) by plotting Ct values versus log DNA copies.

Unless defined otherwise, all technical and scientific terms used herein have the same meaning as commonly understood by one of ordinary skill in the art.

PCR refers to polymerase chain reaction.

Pyrophosphorolysis is the reverse reaction of deoxyribonucleic acid polymerization. In the presence of pyrophosphate, the 3' nucleotide is removed by a polymerase from duplex DNA to generate a triphosphate nucleotide and a 3' unblocked duplex DNA: $[dNMP]_n + PPi \rightarrow [dNMP]_{n-1} + dNTP$ (Deutscher and Kornberg, 1969).

Polymerase or nucleic acid polymerase refers to a polymerase characterized as polymerization or extension of deoxyribonucleic acids.

3' blocked primer refers to an oligonucleotide with a 3' non-extendable nucleotide (3' blocker), such as a dideoxynucleotide or an acycolonucleotide. The 3' nucleotide could not be directly extended, but it can be removed by pyrophosphorolysis and then the unblocked primer can be extended by polymerase.

PAP refers to pyrophosphorolysis activated polymerization.

Bidirectional-PAP (Bi-PAP) is a form of PAP that uses a pair of opposing blocked primers that overlap by one nucleotide at their 30 termini.

Exponential-PAP is a form of PAP that uses a pair of two opposing forward and reverse primers for exponential product accumulation with cycles. At least one primer is blocked primer.

Sensitivity or detection limit is defined as the smallest copy number of a template that generates a detectable product when the blocked primers match the template at the targeted nucleotide, such as the 3' end.

Specificity is defined as the largest copy number of a template that generates an undetectable product when the blocked primers mismatch the template at the targeted nucleotide, such as the 3' end.

Selectivity, the ratio of sensitivity to specificity, is defined as the ability to detect a small number of copies of the matched template in the presence of a large number of copies of mismatched templates without causing false positives.

Thermostable enzyme refers to an enzyme that is heat stable or heat resistant.

TaqFS is a genetic engineered form of Taq polymerase containing G46E and F667Y amino acid changes compared with wild type sequence.

A locus is defined as a short region of nucleotide sequence, such as 40 bp, in genome.

Multiple templates or alleles at one locus mean that at least two templates are located at a short region of nucleotide sequence. The sequence differences among the templates, may be as little as one base substitution, a few base deletion or insertion, and may be located as near as at the same nucleotide. In addition, the alleles may be completely or partially overlapped within the region.

Multiple almost-sequence-identical templates or alleles mean at least two templates, typically located at one locus in genome, among which the sequence differences may be as little as one base substitution, a few base deletion or insertion.

A pair of primers means two opposing forward and reverse primers.

Singleplex-PAP means that one pair of primers amplify one template in a reaction.

Multiplex-PAP means that ≥2 pairs of primers amplify ≥2 potential templates in a reaction.

Multiplex-PAP at multiple loci is a form of multiplex PAP that ≥2 pairs of primers amplify ≥2 potential templates at ≥2 loci in a reaction.

One-Locus-Multiplex-PAP is a form of multiplex PAP that ≥2 pairs of primers amplify ≥2 potential templates at one locus in a reaction.

One-Locus-Duplex-PAP means that 2 pairs of primers amplify 2 potential templates at one locus in a reaction.

One-Locus-Triplex-PAP means that 3 pairs of primers amplify 3 potential templates at one locus in a reaction.

The 5' region of a primer is the 5' part of the primer sequence, such as the ten successive nucleotides from the 5' end.

The 3' region of a primer is the 3' part of the primer sequence, such as the ten successive nucleotides from the 3' end.

Central region of a primer is the middle part of the primer sequence between the 5' region and the 3' region.

5'-perfect-match primer: the 5' region has no artificial mutations and perfectly matches the starting template.

5'-artificial-mismatch primer: artificial mutations are introduced into the 5' region, resulting to mismatch to the starting template.

Artificial mutation means the mutation that is artificially introduced into primer sequences for substitution, typically in the 5' region.

Artificial mismatch is formed between the artificial mutation in the 5' region of 5'-artificial-mismatch primer and the template.

Starting template is the original template before amplification starts, such as that from genomic or plasmid DNA template.

Duplicated template is duplicated from the starting template in amplification and can also be taken as template in later cycles.

Terminology of Real-Time Fluorescence Detection

Baseline is the level of fluorescence signal during initial cycles. The low level can be considered as background or "noise" of the reaction.

Threshold is defined as the level of fluorescence signal that is a significant higher than baseline signal and can distinguish amplification signal from the background.

Ct (threshold cycle) is the cycle number at which the fluorescence signal crosses the threshold.

Amplification efficiency is defined as the percent of template that is amplified by the end of a cycle.

Principle of 5'-Artificial-Mismatch Primers for One-Locus-Multiplex-PAP

In order for multiple pairs of blocked primers to amplify multiple almost-sequence-identical templates or alleles at one locus without inhibitory interaction, a novel design of 5'-artificial-mismatch primers was developed that contain artificial mutations in the 5' regions, as in Examples 2-4.

a) Four Types of Artificial Mismatches Preferred

Mismatches in short DNA duplexes significantly reduce their thermal stabilities, the levels depending on the type of mismatches. The order of thermal stabilities of a total of eight possible mismatches are approximately: G-T>G-G>G-A>C-T>A-A=T-T>A-C=C-C (mismatch G-T=T-G, G-A=A-G, C-T=T-C, and A-C=C-A) (Modrich, 1987) (Aboul-ela, et al., 1985) (Ikuta, et al., 1987).

We prefer four types of mismatches of G-A, C-T, A-A and T-T because 1) their thermal stabilities are medium in the order: they can disrupt the structures of short DNA duplexes, the levels being not too little and not too much, and 2) their thermal stabilities are within a successive range in the order.

b) The Four Types of Mismatches Caused by Six Types of Artificial Mutations

Considering a One-Locus-Multiplex-PAP, at least two pairs of primers are applied to at least two potential templates. We chose six types of artificial mutations of A to C and C to A, T to G and G to T, A to T and T to A in primers, which always lead to the four types of artificial mismatches between the primers and the complementary strands of the starting or duplicated templates. The other six possible types of artificial mutations of A to G and G to A, T to C and C to T, G to C and C to G are not used at all in the design.

The A to C or C to A artificial mutations cause two types of mismatches of C-T and A-G (mismatch C-T=T-C, and A-G=G-A) between the primers and the complementary strands of the starting or duplicated templates. The T to G and G to T artificial mutations cause the same two types of mismatches of G-A and T-C (mismatch G-A=A-G, and T-C=C-T) between the primers and the complementary strands of the starting or duplicated templates. The A to T and T to A artificial mutations cause other two types of mismatches of T-T and A-A between the primers and the complementary strands of the starting or duplicated templates. Thus, a total of four types of mismatches are counted in One-Locus-Multiplex-PAP.

c) The Number of Artificial Mismatches Caused by Artificial Mutations

When artificial mutations of the forward or reverse primers are designed at different nucleotides in the template sequences, the number of mismatches between the 5' region of a primer and the complementary strand of a starting or duplicated template depends on the number of artificial mutations of the primer and on the template. In any case, the minimum number of mismatches between the 5' region of a primer and the complementary strand of a duplicated template is zero, such as in Examples 2-4.

d) Locations of Artificial Mismatches Preferred to Localize in the 5' Region of Primers We prefer to localize artificial mismatches in the 5' regions of primers because 1) besides the types, the locations of mismatches also affect thermal stability of short DNA duplexes (Modrich, 1987) (Piao, et al., 2008), and 2) We found that 28-30mer blocked primers commonly had >90% efficiency of pyrophosphorolysis and extension when mismatches vary from the $1^{st}$ to $12^{th}$ nucleotides from the 5' ends, i.e., the 5' regions. However, they had very low efficiency of pyrophosphorolysis and extension when mismatches are located in the 3' regions, particularly at the 3' ends.

Thus, artificial mutations are preferred to localize in the 5' regions, ranging from the $1^{st}$ to the $12^{th}$ nucleotide from the 5' ends, better ranging from the $3^{rd}$ to $9^{th}$ nucleotide from the 5' ends.

e) Mechanism by Different Numbers of Mismatches Between Different Primers and Different Templates in One-Locus-Multiplex-PAP In a One-Locus-Multiplex-PAP, ≥2 pairs of primers amplify ≥2 potential templates at one locus in a reaction. For a 5'-artificial-mismatch primer, such as each of the forward primers of the first pair, the second pair and the third pair, an artificial mutation is designed into the 5' region. The number of mismatches between the 5' regions and the complementary strands of the starting or duplicated templates varies, such as from zero to 4, depending on annealing of a specific primer to a specific template. Thus, the different numbers of mismatches between different primers and different templates provide the mechanism to reduce inhibitory interaction: 1) the 5' region of a 5'-artificial-mismatch primer matches its corresponding templates more than its competing templates, and 2) a template matches the 5' region of its corresponding 5'-artificial-mismatch primer more than its competing 5'-artificial-mismatch primers, as in Examples 2-4.

Example 1

Materials and Methods
Preparation of Primers

3' ddCMP blocked primers were chemically synthesized in 3'-5' direction and purified by HPLC by Integrated DNA Technologies.

3' ddAMP, ddTMP and ddGMP blocked primers were synthesized enzymatically by adding ddATP, ddTTP and ddGTP to the 3' ends of oligodeoxynucleotides by terminal transferase (Liu and Sommer, 2000; Liu and Sommer, 2002). Then they were purified by 7M urea/16% polyacrylamide gel electrophoresis. The amount of each recovered primer was determined by UV absorbance at 260 nm.

Preparation of Templates

Genomic DNA was extracted from blood white cells using QIAamp Blood Mini Kit according to Qiagen's protocol. Recombinant plasmid DNA was constructed by inserting into pUC57 vector a 100-400 bp target DNA segment which was chemically synthesized or PCR amplified. After transformed into E. coli, the recombinant plasmid DNA was extracted using QIAamp Plasmid Mini Kit according to Qiagen's protocol. The eluted DNA was dissolved in TE buffer (10 mM Tris-HCl, 0.1 mM EDTA, pH8.0) and its amount was determined by UV absorbance at 260 nm.

PAP Reaction

Unless stated otherwise, the PAP reaction mixture of 20 μl contained 88 mM Tris-HCl (pH 8.0 at 25° C.), 10 mM $(NH_4)_2SO_4$, 1.2-2.5 mM $MgCl_2$, 25 μM each dNTPs (dATP, dTTP, dGTP and dCTP), 0.1 μM each primers, 90 μM $Na_4PP_i$, 0.1× SybrGreen I dye, 1-2 units of polymerase, and starting DNA template.

Thermocycling

A Bio-Rad CFX96 real-time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

A cycling entailed 96° C. for 12 seconds, 60° C. for 30 seconds, 64° C. for 30 seconds, and 68° C. for 30 seconds for a total of 40 cycles; or another cycling entailed 96° C. for 12 seconds, 64° C. for 45 seconds, and 68° C. for 45 seconds for a total of 40 cycles. A denaturing step of 96° C. for 2 min was added before the first cycle.

To confirm the amplified product, melting curving analysis was followed from 68° C. to 95° C. with increment 0.5° C. and holding 5 seconds to confirm the specific amplified product.

Serial Dilution Experiment to Determine Amplification Efficiency

In order to determine the amplification efficiency, the template of plasmid or genomic DNA was 10-fold serially diluted from $10^6$ to 10 copies per 20 ul of reaction. In real-time PAP, Ct value was measured for each reaction which is proportional to the amount of amplified product in the early exponential phase of amplification. In addition, melting temperature was measured to confirm the specific amplified product.

Then Ct values are plotted with log DNA copies so that the equation of linear regression, coefficient of determination ($R^2$), and slop can be calculated. The slope is converted into the amplification efficiency by a formula: Efficiency= $10^{(-1/slope)}-1$.

11

Example 2

One-Locus-Duplex-PAP in Exon 19 of the EGFR Gene

In a One-Locus-Duplex-PAP, two pairs of 5'-artificial-mismatch blocked primers COSM6255 and COSM12369 (SEQ ID 15 and 16, 19 and 16) were developed to detect two deletions of del2239_2256, an 18 base deletion COSM6255 (SEQ ID 13), and del2240_2254, a 15 base deletion COSM12369 (SEQ ID 17) in exon 19 of the EGFR gene (Table 2).

For the forward primer (SEQ ID 15) of the first pair COSM6255, two artificial mutations were introduced into the 5' region, i.e., a T to G at the $4^{th}$ nucleotide and an A to C at the $7^{th}$ nucleotide from the 5' end. The 3' end has two nucleotides, CddC, that are specific to the templates COSM6255 (SEQ ID 13 and 14), but mismatch the wildtype and other templates, providing high discrimination. For the reverse primer (SEQ ID 16) of the first pair, it is shared by the second pair of primers and no artificial mutations were introduced (Table 2).

For the forward primer (SEQ ID 19) of the second pair COSM12369, two artificial mutations were introduced into the 5' region, i.e., a T to G at $3^{rd}$ nucleotide, an A to C at $6^{th}$ nucleotide from the 5' end. The 3' end has two nucleotides, CddT, that are specific to the templates COSM12369 (SEQ ID 17 and 18), but mismatch the wildtype and other templates (Table 2).

FIG. 1 shows how the 5'-artificial-mismatch primers work with the two pairs of primers COSM6255 and COSM12369 (SEQ ID No 15 and 16, 19 and 16). Only the 5' regions of primers (SEQ ID 15 and 19) are diagramed with the complementary strands of the starting and duplicated templates COSM6255 (SEQ ID 13 and 14). The number of mismatches varies from zero to 4, depending on combination of the specific primer and template, indicating the mechanism how to reduce the inhibitory interaction among the primers.

Table 3 describes a more complex situation. Rather than amplify one template in FIG. 1, the two pairs of primers COSM6255 and COSM12369 (SEQ ID No 15 and 16, 19 and 16) amplify the templates COM625 and COSM12369 (SEQ NO 13 and 14, 17 and 18) in one reaction. Only the 5' regions of the forward 5'-artificial-mismatch primers (SEQ ID 15 and 19) are counted with the complementary strands of the starting and duplicated templates COM625 and COSM12369 (SEQ NO 13 and 14, 17 and 18). The number and type of mismatches between the 5' regions and the complementary strands of the templates are shown, indicating again the mechanism: 1) a 5'-artificial-mismatch primer matches its corresponding templates more than its competing templates in the 5' region, and 2) a template matches its corresponding 5'-artificial-mismatch primer more than its competing 5'-artificial-mismatch primers in the 5' region.

The One-Locus-Duplex-PAP used the two pairs of primers COSM6255 and COSM12369 (SEQ ID No 15 and 16, 19 and 16) to amplify the potential templates COSM6255 and COSM12369 (SEQ ID 13 and 14, 17 and 18), individually or together (FIG. 2, Table 2). For comparison, the Singleplex-PAP used a pair of primers to amplify its corresponding templates.

To determine the amplification efficiencies, the starting templates were 10-fold serially diluted from $10^6$ to 10 copies per 20 ul of reaction (FIG. 2, Table 2). No inhibitory interaction was observed because the efficiency difference between the Singleplex-PAP and One-locus-Duplex-PAP is <5% to amplify the same template.

Example 3

One-Locus-Triplex-PAP in Exon 18 of the EGFR Gene

In a One-Locus-Triplex-PAP, three pairs of 5'-artificial-mismatch blocked primers COSM6252, COSM6253 and COSM6239 (SEQ ID 22 and 23, 26 and 27, 30 and 31) were developed in exon 18 of the EGFR gene (Table 4).

For each primer, an artificial mutation was introduced into the 5' region (Table 4). For example, for the forward primer (SEQ ID 22) of the first pair COSM6252, an A to C artificial mutation was introduced at the $5^{th}$ nucleotide from the 5' end. For the forward primer (SEQ ID 26) of the second pair COSM6253, a T to G was introduced at $7^{th}$ nucleotide from the 5' end. For the forward primer (SEQ ID 30) of the third pair COSM6239, a T to G was introduced at $7^{th}$ nucleotide from the 5' end.

FIG. 3 and Table 5 show how the 5'-artificial-mismatch primers work with the three pairs of primers COSM6252, COSM6253 and COSM6239 (SEQ ID 22 and 23, 26 and 27, 30 and 31). Only the 5' regions of the forward primers (SEQ ID 22, 26 and 30) are counted with the complementary strands of the corresponding starting and duplicated templates. The number of mismatches between the 5' regions and the complementary strands of the templates varies from zero to 2, depending on combination of the specific primer and template, indicating the mechanism.

In addition, for the first pair of primers COSM6252 (SEQ ID 22 and 23), the 3' ends are specific to the templates COSM6252 (SEQ ID 20 and 21) that contain c.2155G>A substitution in exon 18 of the EGFR gene, but mismatch the wildtype and other templates, providing high discrimination. For the second pair of primers COSM6253 (SEQ ID 26 and 27), the 3' ends are specific to the templates COSM6253 (SEQ ID 24 and 25) that contain c.2155G>T substitution, but mismatch the wildtype and other templates. For the third pair of primers COSM6239 (SEQ ID 30 and 31), the 3' ends are specific to the templates COSM6239 (SEQ ID 28 and 29) that contain c.2156G>C substitution, but mismatch the wildtype and other templates.

The One-Locus-Triplex-PAP used the three pairs of primers COSM6252, COSM6253 and COSM6239 (SEQ ID 22 and 23, 26 and 27, 30 and 31) to amplify the potential templates COSM6252 (SEQ ID 20 and 21), COSM6253 (SEQ ID 24 and 25) and COSM6239 (SEQ ID 28 and 29), individually or together (FIG. 4, Table 4). For comparison, the Singleplex-PAP used a pair of primers to amplify its corresponding template.

Through 10-fold serial dilution of the starting templates, amplification efficiencies of the Singleplex-PAP and One-Locus-Duplex-PAP were determined (FIG. 4, Table 4). No inhibitory interaction was observed by using 5'-artificial-mismatch primers in the One-Locus-Triplex-PAP in exon 18 of the EGFR gene.

Example 4

One-Locus-Triplex-PAP in Exon 2 of the KRAS Gene

In a One-Locus-Triplex-PAP, three pairs of 5'-artificial-mismatch blocked primers COSM518, COSM516 and COSM517 (SEQ ID 34 and 35, 38 and 39, 42 and 43) were developed in exon 2 of the KRAS gene (Table 6).

For each primer, an artificial mutation was introduced into the 5' region (Table 6). For example, for the forward primer (SEQ ID 34) of the first pair COSM518, an A to C artificial mutation was introduced at the 5$^{th}$ nucleotide from the 5' end. For the forward primer (SEQ ID 38) of the second pair COSM516, an A to C was introduced at 7$^{th}$ nucleotide from the 5' end. For the forward primer (SEQ ID 42) of the third pair COSM517, an A to C was introduced at 9$^{th}$ nucleotide from the 5' end.

FIG. 5 and Table 7 show how the 5'-artificial-mismatch primers work with the three pairs of the primers COSM518, COSM516 and COSM517 (SEQ ID 34 and 35, 38 and 39, 42 and 43). Only the 5' regions of the forward primers (SEQ ID 34, 38 and 42) are considered with the complementary strands of the corresponding starting and duplicated templates. The number of mismatches between the 5' regions and the complementary strands of the templates varies from zero to 2, depending on combination of the specific primer and template, indicating the mechanism.

For the first pair of primers COSM518 (SEQ ID 34 and 35), the 3' ends are specific to the templates COSM518 (SEQ ID 32 and 33) that contain c.34G>C substitution in exon 2 of the KRAS gene, but mismatch the wildtype and other templates, providing the high discrimination. For the second pair of primers COSM516 (SEQ ID 38 and 39), the 3' ends are specific to the templates COSM516 (SEQ ID 36 and 37) that contain c.34G>T substitution, but mismatch the wildtype and other templates. For the third pair of primers COSM517 (SEQ ID 42 and 43), the 3' ends are specific to the templates COSM517 (SEQ ID 40 and 41) that contain c.34G>A substitution, but mismatch the wildtype and other templates.

Figure 6:
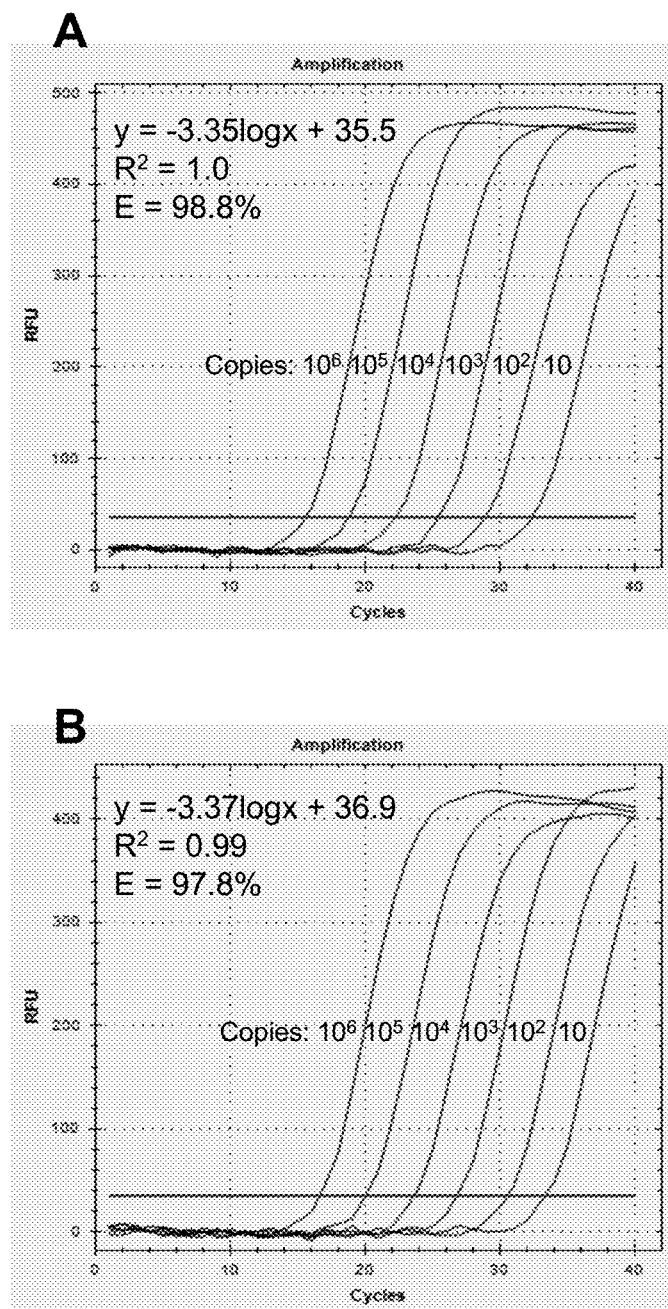
FIG. 6 shows comparison of amplification efficiencies in exon 2 of the KRAS gene. In panel A, Singleplex-PAP used a pair of 5'-artificial-mismatch blocked primers COSM518 (SEQ ID 34 and 35) to amplify the templates COSM518 (SEQ ID 32 and 33) from plasmid DNA (Table 6). In pane B, One-Locus-Triplex-PAP used three pairs of primers COSM518, COSM516 and COSM517 (SEQ ID 34 and 35, 38 and 39, 42 and 43) to amplify the template COSM518 form plasmid DNA (SEQ ID 32 and 33).

The One-Locus-Triplex-PAP used the three pairs of primers COSM518, COSM516 and COSM517 (SEQ ID 34 and 35, 38 and 39, 42 and 43) to amplify the potential templates COSM518 (SEQ ID 32 and 33), COSM516 (SEQ ID 36 and 37) and COSM517 (SEQ ID 40 and 41), individually or together (FIG. 6, Table 6). For comparison, the Singleplex-PAP used a pair of primers to amplify its corresponding template.

Through 10-fold serial dilution of the starting templates, amplification efficiencies of the Singleplex-PAP and One-Locus-Duplex-PAP were determined (FIG. 6, Table 6). No inhibitory interaction was observed by using 5'-artificial-mismatch primers in the One-Locus-Triplex-PAP in exon 2 of the KRAS gene.

REFERENCE

Aboul-ela F, Koh D, Tinoco I, Jr., Martin F H. 1985. Base-base mismatches. Thermodynamics of double helix formation for dCA3XA3G+dCT3YT3G (X, Y=A,C,G,T). Nucleic Acids Res 13(13):4811-24.

Deutscher M P, Kornberg A. 1969. Enzymatic synthesis of deoxyribonucleic acid. 28. The pyrophosphate exchange and pyrophosphorolysis reactions of deoxyribonucleic acid polymerase. J Biol Chem 244(11):3019-28.

Ikuta S, Takagi K, Wallace R B, Itakura K. 1987. Dissociation kinetics of 19 base paired oligonucleotide-DNA duplexes containing different single mismatched base pairs. Nucleic Acids Res 15(2):797-811.

Liu Q, Nguyen V Q, Li X, Sommer S S. 2006. Multiplex dosage pyrophosphorolysis-activated polymerization: application to the detection of heterozygous deletions. Biotechniques 40(5):661-8.

Liu Q, Sommer S S. 2000. Pyrophosphorolysis-activated polymerization (PAP): application to allele-specific amplification. Biotechniques 29(5):1072-1080.

Liu Q, Sommer S S. 2002. Pyrophosphorolysis-activatable oligonucleotides may facilitate detection of rare alleles, mutation scanning and analysis of chromatin structures. Nucleic Acids Res 30(2):598-604.

Liu Q, Sommer S S. 2004a. Detection of extremely rare alleles by bidirectional pyrophosphorolysis-activated polymerization allele-specific amplification (Bi-PAP-A): measurement of mutation load in mammalian tissues. Biotechniques 36(1):156-66.

Liu Q, Sommer S S. 2004b. PAP: detection of ultra rare mutations depends on P* oligonucleotides: "sleeping beauties" awakened by the kiss of pyrophosphorolysis. Hum Mutat 23(5):426-36.

Liu Q, Sommer S S. 2004c. Pyrophosphorolysis by Type II DNA polymerases: implications for pyrophosphorolysis-activated polymerization. Anal Biochem 324(1):22-8.

Modrich P. 1987. DNA mismatch correction. Annu Rev Biochem 56:435-66.

Piao X, Sun L, Zhang T, Gan Y, Guan Y. 2008. Effects of mismatches and insertions on discrimination accuracy of nucleic acid probes. Acta Biochim Pol 55(4):713-20.

TABLE 2

5'-artificial-mismatch primers for One-Locus-Duplex-PAP in exon 19 of the EGFR gene

| # | COSMIC ID [a,b] | Target [b] | Template and primer | Sequence (5' to 3') (SEQ ID NO) | Artificial mutation [f] Type | nt from the 5' end | Amplification efficiency PAP [g] | PAP [h] | Inhibition in Duplex-Pap [i] |
|---|---|---|---|---|---|---|---|---|---|
| 1 | COSM 6255 | del2239_2256 | Starting Template [c] | 5'agttaaaattcccgtcgctatcaaggaa ccgaaagccaacaaggaaatcctcgatgtg agtttc3' (13) | | | 99.4% | 99.6% | 0.2% [i], No |
| | | | Duplicated template [c] | 5'agtGaaCattcccgtcgctatcaaggaa ccgaaagccaacaaggaaatcctcgatgtg agtttt3' (14) | | | | | |
| | | | Forward primer [d] | 5'AGTGAACATTCCCGTCGCTA TCAAGGAACddC (15) | T to G, A to C | 4, 7 | | | |
| | | | Reverse primer [d] | 5'GAAACTCACATCGAGGATTT CCCTTGTTGGddC (16) | | | | | |
| 2 | COSM 12369 | del2240_2254 | Starting Template | 5'agttaaaattcccgtcgctatcaaggaa tctccgaaagccaacaaggaaatcctcgat gtgagtttc3' (17) | | | 96.7% | 95.2% | 1.5%, No |

TABLE 2-continued

5'-artificial-mismatch primers for One-Locus-Duplex-PAP in exon 19 of the EGFR gene

| # | COSMIC ID [a,b] | Target [b] | Template and primer | Sequence (5' to 3') (SEQ ID NO) | Artificial mutation [f] Type | nt from the 5'end | Amplification efficiency PAP [g] | PAP [h] | Inhibition in Duplex-Pap [i] |
|---|---|---|---|---|---|---|---|---|---|
| | | | Duplicated template | 5'agGtaCaattcccgtcgctatcaaggaa tctccgaaagccaacaaggaaatcctcgat gtgagtttc3' (18) | | | | | |
| | | | Forward primer | 5'AGGTACAATTCCCGTCGCTA TCAAGGAATC<u>ddT</u> (19) | T to G, A to C | 3, 6 | | | |
| | | | Reverse primer [e] | 5'GAAACTCACATCGAGGATTT CCTTGTTGG<u>ddC</u> (16) | | | | | |

Footnotes of Table 2.
[a] From www.sanger.ac.uk/genetics/CGP/cosmic/
[b] COSM6255 contains del2239_2256 deletion, and COSM 12369 contains del2240 2254 deletion in exon 19 of the EGFR gene.
[c] Only the downstream strand of the template is shown. For the duplicated template, the two upper, bold and underlined cases are corresponding artificial mutations duplicated from the 5'-artificial-mismatch primer, and can be taken as template in later cycles.
[d] Forward primer is a 5'-artificial-mismatch primer in which two artificial mutations G and C are indicated as bold and underlined cases. In addition, the underlined <u>CddC</u> are two nucleotides at the 3' end that are specific to COSM6255 template, but mismatch the wildtype sequence.
[e] Reverse primer is used for both pairs of primers, and no artificial mutations are introduced for this primer.
[f] Artificial mutation is indicated with the type and location from the 5' end of a primer.
[g] In the Singleplex-PAP, the first pair of primers amplified the first template in a first reaction, and the second pair of primers amplified the second template in a second reaction to determine their amplification efficiencies.
[h] In the One-Locus-Duplex-PAP, the two pairs of primers amplified the first template in a first reaction and the second template in a second reaction, respectively.
[i] Inhibition is called Yes if the efficiency difference between the Singleplex-PAP and One-locus-Duplex-PAP is ≥5% to amplify the same template, or No if it is <5%. 0.2% is the efficiency difference between the Singleplex-PAP and One-Locus-Duplex-PAP.

TABLE 3

The number and type of mismatches between the 5' regions of 5'-artificial-mismatch primers and the templates in exon 19 of the EGFR gene by One-Locus-Duplex-PAP

| | | | Artificial mutation in the 5' region of the forward primer [a] | |
|---|---|---|---|---|
| # | Complimentary strand of the template | | COSM6255 T to G at $4^{th}$ nt, A to C at $7^{th}$ nt [b] | COSM12369 T to G at $3^{rd}$ nt, A to C at $6^{th}$ nt |
| 1 | COSM 6255 | Starting [a] | 2, G-A, C-T [c] | 2, G-A, C-T |
| | | Duplicated [a] | 0 | 4, G-A, T-C, C-T, A-G |
| 2 | COSM 12369 | Starting | 2, G-A, C-T | 2, G-A, C-T |
| | | Duplicated | 4, T-C, G-A, A-G, C-T | 0 |

Footnotes of Table 3.
[a] Only the 5' regions of the forward 5'-artificial-mismatch primers and the complementary strands of the starting and duplicated templates are considered in the One-Locus-Duplex-PAP.
[b] T to G at $4^{th}$ nt, A to C at $7^{th}$ nt means that two artificial mutations of a T to G artificial mutation at the $4^{th}$ nucleotide from the 5' end, and an A to C artificial mutation at the $7^{th}$ nucleotide from the 5' end are contained in the 5' region of the forward 5'-artificial-mismatch primer COSM6255.
[c] 2 means two artificial mismatches. For example, a G-A mismatch is formed between the 5' region of the forward 5'-artificial-mismatch primer COSM6255 and the complementary strand of the starting template COSM6255. The artificial mismatch is the $4^{th}$ nucleotide calculated from the 5' end of the primer.

TABLE 4

5'-artificial-mismatch primers for One-Locus-Triplex-PAP in exon 18 of the EGFR gene

| # | COSMIC ID [a] | Target [a] | Template and primer | Sequence (5' to 3') (SEQ ID NO) | 5' Artificial mismatch Type | nt from the 5'end | Amplification efficiency Single-plex-PAP [b] | Triplex-PAP [c] | Inhibition in Triplex PAP |
|---|---|---|---|---|---|---|---|---|---|
| 1 | COSM 6252 | c.2155 G > A | Starting Template | 5'actgaattcaaaaagatcaaagtgct gAgctccggtgcgttccggcacggtgta ta3' (20) | | | 99.9% | 101.3% | 0.4%, No |
| | | | Duplicated template | 5'actgCattcaaaaagatcaaagtgct gAgctccggtgcgttcggcacTgtgtat a3' (21) | | | | | |

TABLE 4-continued

5'-artificial-mismatch primers for One-Locus-Triplex-PAP in exon 18 of the EGFR gene

| # | COSMIC ID [a] | Target [a] | Template and primer | Sequence (5' to 3') (SEQ ID NO) | 5' Artificial mismatch Type | nt from the 5' end | Amplification efficiency Singleplex-PAP [b] | Triplex-PAP [c] | Inhibition in Triplex PAP |
|---|---|---|---|---|---|---|---|---|---|
| | | | Forward primer [d] | 5'ACTGCATTCAAAAAGATCA AAGTGCTG<u>dd</u>A (22) | A to C | 5 | | | |
| | | | Reverse primer [d] | 5'TATACACAGTGCCGAACGC ACCGGAGC<u>dd</u>T (23) | C to A | 8 | | | |
| 2 | COSM 6253 | c.2155 G > T | Starting Template | 5'actgaattcaaaaagatcaaagtgct gTgctccggtgcgttcggcacggtgtat a3' (24) | | | 98.1% | 95.6% | 2.5%, No |
| | | | Duplicated template | 5'actgaaGtcaaaaagatcaaagtgct gTgctccggtgcgttcggcaAggtgtat a3' (25) | | | | | |
| | | | Forward primer | 5'ACTGAGTCAAAAAGATCA AAGTGCT<u>dd</u>T (26) | T to G | 7 | | | |
| | | | Reverse primer | 5'TATACACCTTGCCGAACGCA CCGGAGC<u>dd</u>A (27) | G to T | 9 | | | |
| 3 | COSM 6239 | c.2156 G > C | Starting Template | 5'ctgaattcaaaaagatcaaagtgctg gCctccggtgcgttcggcacggtgtata a3' (28) | | | 97.3% | 97.0% | 0.3%, No |
| | | | Duplicated template | 5'ctgaatGcaaaaagatcaaagtgctg tgCccggtgcgttcggcacgAtgtata a3' (29) | | | | | |
| | | | Forward primer | 5'CTGAATGCAAAAAGATCAA AGTGCTGC<u>dd</u>C (30) | T to G | 7 | | | |
| | | | Reverse primer | 5'TTATACAACGTGCCGAACGC ACCGGAG<u>dd</u>G (31) | C to A | 8 | | | |

Footnotes of Table 4.
[a] COSM6252 contains c.2155G > A substitution, COSM6253 contains c.2155G > T substitution, and COSM6239 contains c.2156G > C substitution in exon 18 of the EGFR gene. The three substitutions are located at two neighboring nucleotides in the sequences.?
[b] In the Singleplex-PAP, the first pair of primers amplified the first template in a first reaction, the second pair of primers amplified the second template in a second reaction, and the third pair of primers amplified the third template in a third reaction to determine their amplification efficiencies.?
[c] In the One-Locus-Triplex-PAP, the three pairs of primers amplified the first template in a first reaction, the second template in a second reaction, and the third template in a third reaction, respectively.?

TABLE 5

The number and type of mismatches between the 5' regions of 5'-artificial-mismatch primers and the templates in exon 18 of the EGFR gene by One-Locus-Triplex-PAP [a]

| | | | Artificial mutation in the 5' region of the forward primer | | |
|---|---|---|---|---|---|
| # | Cpmplimentary strand of the template | | COSM6252 A to C at 5<sup>th</sup> nt | COSM6253 T to G at 7<sup>th</sup> nt [b] | COSM6239 T to G at 7<sup>th</sup> nt [b] |
| 1 | COSM6252 | Starting | 1, C-T | 1, G-A | 1, G-A |
| | | Duplicated | 0 | 2, A-G, G-A | 2, A-G, G-A |
| 2 | COSM6253 | Starting | 1, C-T | 1, G-A | 1, G-A |
| | | Duplicated | 2, C-T, T-C | 0 | 2, T-C, G-A |
| 3 | COSM6239 | Starting | 1, C-T | 1, G-A | 1, G-A |
| | | Duplicated | 2, C-T, T-C | 2, G-A, T-C | 0 |

Footnotes of Table 5.
[a] The One-Locus-Triplex-PAP used the three pairs of primers COSM6252, COSM6253 and COSM6239 (SEQ ID 22 and 23, 26 and 27, 30 and 31) to amplify the templates COSM6252 (SEQ ID 20 and 21), COSM6253 (SEQ ID 24 and 25) and COSM6239 (SEQ ID 28 and 29) in a reaction.
[b] Although the two artificial mutations of the two forward primers are at the same location calculated from their 5' ends, they are located at different nucleotides in the template sequences.

TABLE 6

5'-artificial-mismatch primers for One-Locus-Triplex-PAP in exon 2 of the KRAS gene

| # | COS-MIC ID [a] | Target [a] | Template and primer | Sequence (5' to 3') (SEQ ID NO) | 5' Artificial mismatch Type | nt from the 5'end | Amplification efficiency Single-plex-PAP [b] | Triplex-PAP [c] | Inhibition in Triplex PAP |
|---|---|---|---|---|---|---|---|---|---|
| 1 | COSM 518 | c.34 G > C | Starting Template | 5'ctgaatataaacttgtggtagttggagc tCgtggcgtaggcaagagtgccttgacgat a3' (32) | | | 98.8% | 97.8% | 1.0%, No |
| | | | Duplicated template | 5'ctgaCtataaacttgtggtagttggagc tCgtggcgtaggcaagagtgcAttgacgat a3' (33) | | | | | |
| | | | Forward primer [d] | 5'CTGACTATAAACTTGTGGTAG TTGGAGCTddC (34) | A to C | 5 | | | |
| | | | Reverse primer [d] | 5'TATCGTCAATGCACTCTTGCC TACGCCACddG (35) | G to T | 10 | | | |
| 2 | COSM 516 | c.3.4 G > T | Starting Template | 5'ctgaatataaacttgtggtagttggagc Tgtggcgtaggcaagagtgccttgacgata 3' (36) | | | 97.5% | 98.9% | 1.4%, No |
| | | | Duplicated template | 5'ctgaatCtaaacttgtggtagttggagc tTgtggcgtaggcaagagtgccttTacgat a3' (37) | | | | | |
| | | | Forward primer | 5'CTGAATCTAAACTTGTGTGGTAG AAGTGCTddT (38) | A to C | 7 | | | |
| | | | Reverse primer | 5'TATCGTAAAGGCACTCTTGCC TACGCCACddA (39) | C to A | 7 | | | |
| 3 | COSM 517 | c.34 G > A | Starting Template | 5'ctgaatataaacttgtggtagttggagc tAgtggcgtaggcaagagtgccttgacgat a3' (40) | | | 98.8% | 100.1% | 1.3%, No |
| | | | Duplicated template | 5'ctgaatatCaacttgtggtagttggagc tAgtggcgtaggcaagagtgccttgTcgat a3' (41) | | | | | |
| | | | Forward primer | 5'CTGAATATCAACTTGTGGTAG TTGGAGCTddC (42) | A to C | 9 | | | |
| | | | Reverse primer | 5'TATCGACAAGGCACTCTTGCC TACGCCACddT (43) | T to A | 6 | | | |

Footnotes of Table 6.
[a] COSM518 contains c.34G > C substitution, COSM516 contains c.34G > T substitution, COSM517 contains c.34G > A substitution in exon 2 of the KRAS gene. The three substitutions are located at two neighboring nucleotides in the sequences.
[b] In the Singleplex-PAP, the first pair of primers amplified the first template in a first reaction, the second pair of primers amplified the second template in a second reaction, and the third pair of primers amplified the third template in a third reaction to determine their amplification efficiencies.
[c] In the One-Locus-Triplex-PAP, the three pairs of primers amplified the first template in a first reaction, the second template in a second reaction, and the third template in a third reaction.

TABLE 7

The number and type of mismatches between the 5' regions of 5'-artificial-mismatch primers and the templates in exon 2 of the KRAS gene by One-Locus-Triplex-PAP [a]

| | | | Artificial mutation in the 5' region of the forward primer | | |
|---|---|---|---|---|---|
| # | | Cpmplimentary strand of the template | COSM518 A to C at 5$^{th}$ nt | COSM516 A to C at 7$^{th}$ nt | COSM517 A to C at 9$^{th}$ nt |
| 1 | COSM 518 | Starting | 1, C-T | 1, C-T | 1, C-T |
| | | Duplicated | 0 | 2, A-G, C-T | 2, A-G, C-T |
| 2 | COSM 516 | Starting | 1, C-T | 1, C-T | 1, C-T |
| | | Duplicated | 2, C-T, A-G | 0 | 2, A-G, C-T |
| 3 | COSM 517 | Starting | 1, C-T | 1, C-T | 1, C-T |
| | | Duplicated | 2, C-T, A-G | 2, C-T, A-G | 0 |

Footnotes of Table 7.
[a] The One-Locus-Triplex-PAP used the three pairs of primers COSM518, COSM516 and COSM517 (SEQ ID 34 and 35, 38 and 39, 42 and 43) to amplify the templates COSM518 (SEQ ID 32 and 33), COSM516 (SEQ ID 36 and 37) and COSM517 (SEQ ID 40 and 41) in a reaction.

The invention claimed is:

1. A plurality of pairs of forward and reverse blocked primers for pyrophosphorolysis activated polymerization to amplify a plurality of potential templates in one reaction, wherein the blocked primers, with non-extendable, blocked nucleotides at their 3' ends, are activated by pyrophosphorolysis to produce a 3' unblocked primers and then extended by polymerization, both of which reactions are catalyzed by a polymerase, and wherein the template sequences are located at one locus, i.e., a short region of nucleotide sequence, in a genome and have at least one nucleotide variance from each other, comprising:
 a) a first pair of forward and reverse primers to amplify a first template, wherein the forward primer or reverse primer is designed to introduce at least one artificial mutation into its 5' region, forming one or two artificial mismatch between the 5' region and its template, and
 b) a second pair of forward and reverse primers to amplify a second template which is located at the same locus as the first template but contains at least one nucleotide variance from the first template, wherein the forward or reverse primer in the same direction as the above 5' mutated primer in the first pair is designed to introduce at least one artificial mutation into its 5' region, forming one or two artificial mismatch between the 5' region and its template, and
 wherein in the template sequences, the artificial mutations of the 5' mutated primers in the first pair and in the second pair are located at different nucleotides at the locus of the genome, whereby inhibitory interactions among the primers are substantially reduced in the reaction.

2. The plurality of pairs of forward and reverse blocked primers of claim 1, further comprising a third pair of forward and reverse primers to amplify a third template which is located at the same locus as the first and second templates but contains at least one nucleotide variance from each of the first and second templates, wherein the forward or reverse primer in the same direction as the above 5' mutated primer in the first pair is designed to introduce at least one artificial mutation into its 5' region, wherein in the template sequences, the artificial mutations of the 5' mutated primers in the first pair, the second pair and the third pair are located at different nucleotides at the locus of the genome.

3. The plurality of pairs of forward and reverse blocked primers of claim 1, further comprising:
   c) the first pair of forward and reverse primers, wherein the other of the forward and reverse primers is designed to introduce at least one artificial mutation into the 5' region, and
   d) the second pair of forward and reverse primers, wherein the other of the forward and reverse primers is designed to introduce at least one artificial mutation into the 5' region,
   wherein in the template sequences, the artificial mutations of the 5' mutated primers in the first pair and the second pair are located at different nucleotides at the locus of the genome.

4. The plurality of pairs of forward and reverse blocked primers of claim 1, wherein the 3' regions of the first pair of primers match the first template but mismatch the second template, and the 3' regions of the second pair of primers match the second template but mismatch the first template, and wherein the templates are located at the same locus but contain at least one nucleotide variance from each other.

5. The plurality of pairs of forward and reverse blocked primers of claim 1, wherein one or two artificial mutation is introduced into the 5' region of the forward or reverse primer in the first pair, forming one or two artificial mismatch between the 5' region and its template.

6. The plurality of pairs of forward and reverse blocked primers of claim 1, wherein one or two artificial mutations are introduced into the 5' region of the forward or reverse primer in the second pair, forming one or two artificial mismatch between the 5' region and its template.

7. The plurality of pairs of forward and reverse blocked primers of claim 1, wherein the artificial mutations of the 5' mutated primer in each of the first and second pairs is selected from the group consisting of six types of A to C, C to A, T to G, G to T, A to T, and T to A mutations.

8. The plurality of pairs of forward and reverse blocked primers of claim 1, wherein the artificial mutations of the 5' mutated primer in each of the first and second pairs result in one of the four types of mismatches of G-A, C-T, A-A, and T-T between the 5' regions of the 5' mutated primers and the complementary strands of the templates.

9. The plurality of pairs of forward and reverse blocked primers of claim 1, wherein the artificial mutations of the 5' mutated primer in any of the first and second pairs is selected from the group consisting of four types of A to C, C to A, T to G, and G to T mutations.

10. The plurality of pairs of forward and reverse blocked primers of claim 1, wherein the artificial mutations of the 5' mutated primer in any of the first and second pairs is selected from the group consisting of two types of A to T and T to A mutations.

11. The plurality of pairs of forward and reverse blocked primers of claim 1, the 5' regions of the 5' mutated primers in the first and second pairs range from the first to the twelfth nucleotide from the 5' ends, including the nucleotides at the 5' ends assigned as the first nucleotides from the 5' ends.

12. The plurality of pairs of forward and reverse blocked primers of claim 1, the 5' regions of the 5' mutated primers in the first and second pairs range from the third to the ninth nucleotide from the 5' ends.

13. The plurality of pairs of forward and reverse blocked primers of claim 1, wherein the artificial mutations of the 5' mutated primers in the first and second pairs are at different nucleotides at the locus in the genome.

14. The plurality of pairs of forward and reverse blocked primers of claim 1, wherein the first and second template sequences are completely or partially overlapped in the locus.

15. The plurality of pairs of forward and reverse blocked primers of claim 1, wherein the first and second templates contain at least one nucleotide variance from each other but are located at the same locus in the genome.

16. The plurality of pairs of forward and reverse blocked primers of claim 1, wherein the template sequences are located at one locus, i.e., a short region of nucleotide sequence, wherein said short region of nucleotide sequence is 40 base pairs in length.

* * * * *